United States Patent
Corma Canós et al.

(10) Patent No.: US 10,486,975 B2
(45) Date of Patent: Nov. 26, 2019

(54) SYNTHESIS OF ZEOLITE WITH THE CHA CRYSTAL STRUCTURE, SYNTHESIS PROCESS AND USE THEREOF FOR CATALYTIC APPLICATIONS

(71) Applicants: Consejo Superior de Investigaciones Científicas (CSIC), Madrid (ES); Universitat Politècnica de València, Valencia (ES)

(72) Inventors: Avelino Corma Canós, Valencia (ES); Manuel Moliner Marín, Valencia (ES); Nuria Martín García, Valencia (ES)

(73) Assignees: Consejo Superior de Investigaciones Científicas, Madrid (ES); Universitat Politècnica de València, Valencia (ES)

(*) Notice: Subject to any disclaimer, the term of this patent is extended or adjusted under 35 U.S.C. 154(b) by 0 days.

(21) Appl. No.: 16/396,885

(22) Filed: Apr. 29, 2019

(65) Prior Publication Data

US 2019/0248663 A1   Aug. 15, 2019

Related U.S. Application Data

(63) Continuation of application No. 15/533,913, filed as application No. PCT/EP2015/079425 on Dec. 11, 2015, now Pat. No. 10,322,939.

(30) Foreign Application Priority Data

Dec. 17, 2014 (ES) .................................. 201431861

(51) Int. Cl.
*C01B 39/48* (2006.01)
*B01J 29/70* (2006.01)
(Continued)

(52) U.S. Cl.
CPC .......... *C01B 39/48* (2013.01); *B01D 53/9418* (2013.01); *B01J 29/7015* (2013.01);
(Continued)

(58) Field of Classification Search
CPC ..... C01B 39/04; C01B 39/48; B01L 29/7015; B01L 29/723; B01D 53/9418; C07C 1/20; C07C 2529/70; C07C 2529/72
See application file for complete search history.

(56) References Cited

U.S. PATENT DOCUMENTS

| 3,030,181 A | 4/1962 | Milton et al. |
| 3,832,449 A | 8/1974 | Rosinski et al. |

(Continued)

FOREIGN PATENT DOCUMENTS

| CN | 103118981 A | 5/2013 |
| CN | 104108726 A | 10/2014 |

(Continued)

OTHER PUBLICATIONS

First Office Action received in CN 201580069314X dated Aug. 31, 2018.

(Continued)

*Primary Examiner* — David M Brunsman
(74) *Attorney, Agent, or Firm* — Suzannah K. Sundby, Esq.; Canady + Lortz LLP

(57) ABSTRACT

Disclosed is a synthesis process of a crystalline material with the CHA structure, which comprises the following steps: i) Preparation of a mixture that comprises one source of water, one source of a tetravalent element Y, one source of an alkaline or alkaline earth cation (A), one source of a trivalent element X, and one organic molecule (OSDA1) with the structure $[R^1R^2R^3R^4N^+]Q^-$, being the molar composition: n $X_2O_3$:$YO_2$:a A:m OSDA1:z $H_2O$, ii) crystalli-
(Continued)

sation of the mixture obtained in i) in a reactor, iii) recovery of the crystalline material obtained in ii).

25 Claims, 1 Drawing Sheet

(51) Int. Cl.
    *B01D 53/94*      (2006.01)
    *B01J 29/76*      (2006.01)
    *C01B 39/02*      (2006.01)
    *C07C 1/20*      (2006.01)
    *F01N 3/20*      (2006.01)

(52) U.S. Cl.
    CPC ........... *B01J 29/763* (2013.01); *C01B 39/026* (2013.01); *C07C 1/20* (2013.01); *B01D 2251/2062* (2013.01); *B01D 2255/20761* (2013.01); *B01D 2255/50* (2013.01); *B01J 2229/186* (2013.01); *C07C 2529/70* (2013.01); *C07C 2529/72* (2013.01); *F01N 3/2066* (2013.01); *F01N 2370/04* (2013.01)

(56) References Cited

U.S. PATENT DOCUMENTS

| | | | |
|---|---|---|---|
| 4,440,871 | A | 4/1984 | Lok et al. |
| 4,544,538 | A | 10/1985 | Zones |
| 5,026,532 | A | 6/1991 | Gaffney et al. |
| 8,007,764 | B2 | 8/2011 | Miller et al. |
| 10,322,939 | B2 * | 6/2019 | Corma Canos ....... C01B 39/026 |
| 2004/0138051 | A1 | 7/2004 | Shan et al. |
| 2008/0045767 | A1 | 2/2008 | Cao et al. |
| 2008/0075656 | A1 | 3/2008 | Zones |
| 2008/0159951 | A1 | 3/2008 | Miller et al. |
| 2011/0020204 | A1 | 1/2011 | Bull et al. |
| 2011/0312486 | A1 | 12/2011 | Yilmaz et al. |
| 2014/0140921 | A1 | 5/2014 | Burton et al. |
| 2018/0079650 | A1 | 3/2018 | Corma Canos et al. |

FOREIGN PATENT DOCUMENTS

| | | |
|---|---|---|
| EP | 3381865 A1 | 10/2018 |
| GB | 868846 A | 5/1961 |
| JP | 2012096956 A | 5/2012 |
| WO | 2010114996 A2 | 10/2010 |
| WO | 2011064186 A1 | 6/2011 |
| WO | 2013035054 A1 | 3/2013 |
| WO | 2013182974 A1 | 12/2013 |

OTHER PUBLICATIONS

Concepcion, et al., "Preparation and characterization of Mg-containing AFI and chabazite-type materials", Jan. 1996, pp. 56-64, vol. 16, No. 1, Publisher: Zeolites.

Extended European Search report received in EP18190792 dated Dec. 21, 2018.

Extended European Search report received in EP181907973 dated Jan. 4, 2019.

Search Report and Written Opinion received in ES P201431861, dated Apr. 25, 2016.

Itakura et al., "Synthesis of high-silica CHA type zeolite by interzeolite conversion of FAU type zeolite in the presence of seed crystals", Mar. 24, 2011, pp. 91-96, vol. 144, No. 1-3, Publisher: Microporous and Mesoporous Materials.

Itakura, et al., "Synthesis of High-silica CHA Zeolite from FAU Zeolite in the Presence of Benzyltrimethylammonium Hydroxide", Jul. 26, 2008, pp. 908-909, vol. 37, No. 9, Publisher: Chemistry Letters.

Limin, et al., "Designed copperamine complex as an efficient template for one-pot synthesis of Cu-SSZ-13 zeolite with excellent activity for selective catalytic . . . ", May 31, 2011, pp. 9789-9791, vol. 47, Publisher: Chem. Commun.

Yamanaka et al., "Acid stability evaluation of CHA-type zeolites synthesized by interzeolite conversion of FAU-type zeolite and their membrane application . . . ", Mar. 23, 2012, pp. 141-147, vol. 158, Publisher: Microporous and Mesoporous Materials.

\* cited by examiner

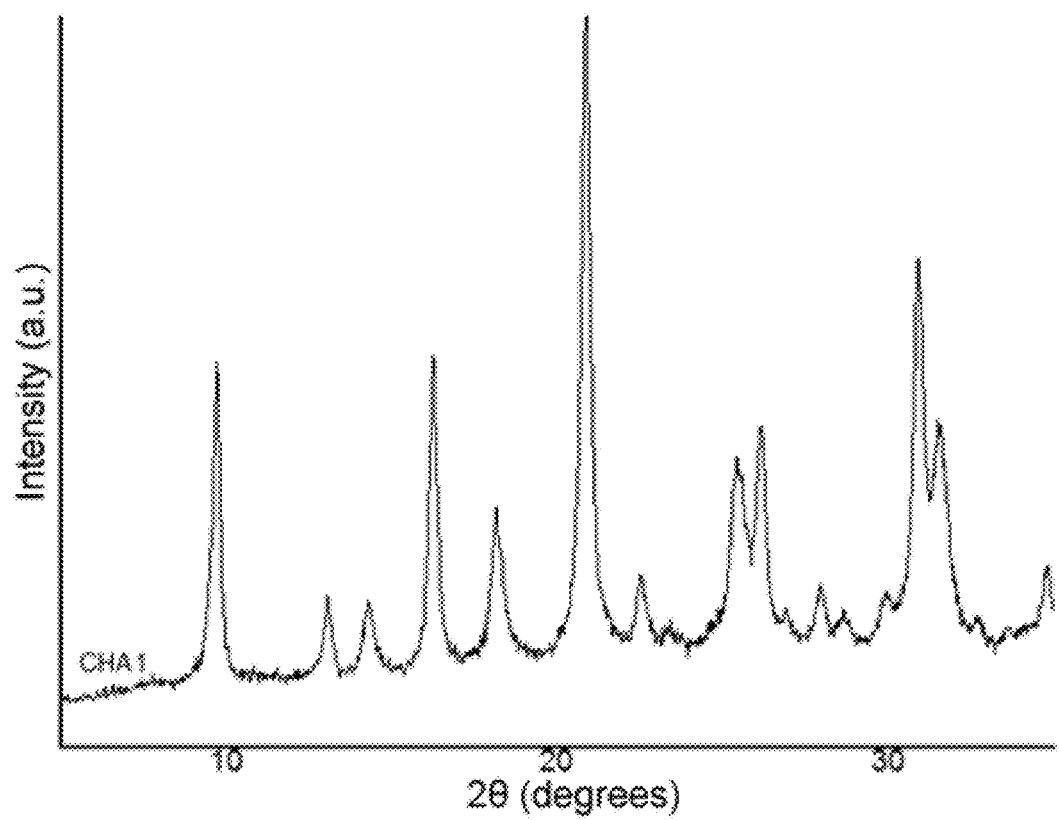

SYNTHESIS OF ZEOLITE WITH THE CHA CRYSTAL STRUCTURE, SYNTHESIS PROCESS AND USE THEREOF FOR CATALYTIC APPLICATIONS

This application is a continuation of Ser. No. 15/533,913, now U.S. patent Ser. No. 10/322,939, which is a 371 filing of PCT/EP2015/079425, filed Dec. 11, 2015.

FIELD OF THE INVENTION

The present invention relates to a new synthesis process of zeolite with the chabazite crystal structure, as well as to the use of the zeolite material synthesised according to the present synthesis process as a catalyst.

BACKGROUND

Zeolites, or molecular sieves, are described as materials formed by $TO_4$ tetrahedra (T=Si, Al, P, Ge, B, Ti, Sn, etc.), interconnected by oxygen atoms, to create pores and cavities of uniform size and shape over the molecular range. These zeolite materials have important applications as catalysts, adsorbents or ion exchangers, amongst others.

Zeolites may be classified on the basis of the size of their channels and pores. In this regard, zeolites with channels limited by 8-T atoms are called "small-pore zeolites" (openings of about 4 Å), zeolites with channels limited by 10-T atoms are "medium-pore zeolites" (openings of about 5.5 Å), those with channels limited by 12-T atoms are "large-pore zeolites" (openings of about 7 Å), and, finally, zeolites with channels limited by more than 12-T atoms are called "extra-large-pore zeolites" (openings greater than 7 Å).

Amongst the more than 200 zeolite structures accepted by the International Zeolite Association (IZA), the chabazite crystal structure is one of the most interesting, due to its use in many diverse applications, most noteworthy as a heterogeneous catalyst in methanol-to-olefins processes (MTO) and in the selective catalytic reduction (SCR) of NOx.

The IZA has assigned the code CHA to the molecular sieve chabazite, which has a crystal structure formed by a tri-directional system of small pores interconnected by large cavities. The CHA structure has been synthesised with various chemical compositions, most noteworthy as an aluminosilicate ("SSZ-13"; Zones, U.S. Pat. No. 4,544,538, 1985, assigned to Chevron) or silicoaluminophosphate ("SAPO-34"; Lok et al., U.S. Pat. No. 4,440,871, 1984, assigned to UOP).

In general, it may be said that aluminosilicates show higher hydrothermal stability and better acidic properties than homologous silicoaluminophosphates (Katada et al., J. Phys. Chem. C., 2011, 115, 22505). Consequently, the synthesis of the CHA structure in aluminosilicate form, in an economical manner and with good physical-chemical properties, would be of great interest for application in industrial processes.

Chabazite is a natural zeolite that has the following chemical composition: $Ca_6Al_{12}Si_{24}O_{72}$. In addition to the natural form of chabazite, this zeolite structure has been synthesised in the laboratory using different inorganic alkaline cations as inorganic structure-directing agents (SDAs). Thus, the following syntheses have been disclosed: zeolite K-G (J. Chem. Soc., 1956, 2822), which is a chabazite synthesised in the presence of potassium cations and has an Si/Al ratio of 1.1-2.1; zeolite D (British Patent 868846, 1961), which is a chabazite synthesised in the presence of sodium-potassium cations and has an Si/Al ratio of 2.2-2.5; and zeolite R (U.S. Pat. No. 3,030,181, 1962, assigned to Union Carbide), which has an Si/Al ratio of 1.7-1.8.

Most likely, the first use of organic structure-directing agents (OSDAs) in the synthesis of the zeolite chabazite was disclosed by Tsitsishrili et al. (Soobsch. Akad. Nauk. Cruz, SSR, 1980, 97, 621), who show the presence of tetramethylammonium (TMA) cations in the reaction mixture $K_2O$—$Na_2O$—$SiO_2$—$Al_2O_3$—$H_2O$. However, the Si/Al ratio obtained in the final solid is very low (Si/Al ~2.1). The article discloses that the presence of TMA in the synthesis medium seems to affect the crystallisation of CHA, but said organic molecule is not incorporated into the synthesised material.

In general, aluminosilicates with a low Si/Al ratio (lower than 5) exhibit low hydrothermal stability. Consequently, in order to increase said Si/Al ratio in the synthesis of CHA, larger OSDAs, such as N,N,N-tri-alkyl-1-adamantylammonium, N-alkyl-3-quinuclidinol and/or N,N,-tri-alkyl-exoaminonorbornane (Zones, U.S. Pat. No. 4,544,538, 1985, assigned to Chevron), were introduced into the synthesis medium. Using these OSDAs, the zeolite CHA is obtained with Si/Al ratios ranging between 4-25, which is called SSZ-13.

The preferred OSDA for the synthesis of the zeolite SSZ-13 is the N,N,N-tri-methyl-1-adamantammonium (TMAdA) cation. However, said OSDA has a high cost. This high cost may limit the commercial use of the zeolite SSZ-13 in industrial processes. Therefore, the synthesis of the zeolite SSZ-13 using more economical OSDAs would be of great interest for potential commercial applications of said zeolite.

An alternative for reducing the content of the TMAdA cation in the preparation of the zeolite SSZ-13 involves introducing mixtures of TMAdA with another, more economical OSDA, such as benzyltrimethylammonium (Zones, U.S. Patent 2008/0075656, 2008, assigned to Chevron). In this invention, the TMAdA content is significantly reduced by introducing the benzyltrimethylammonium cation into the synthesis medium. Despite the cost reduction when preparing the zeolite SSZ-13 using these mixtures of OSDAs, the presence of the TMAdA cation, which has a high cost, is still necessary.

Similarly, the use of mixtures of the OSDAs TMAdA and tetramethylammonium (TMA) in the synthesis medium has been proposed to synthesise the aluminosilicate form of CHA (Bull et al., WO2011/064186, 2011, assigned to BASF). Despite the cost reduction when preparing the zeolite SSZ-13 using these mixtures of OSDAs, the presence of the TMAdA cation, which has a high cost, is still necessary.

Recently, the synthesis of the aluminosilicate form of CHA using new, more economical organic molecules than the original OSDA TMAdA as the only OSDAs in the synthesis medium has been disclosed. Said organic molecules are benzyltrimethylammonium (Miller et al., U.S. Pat. No. 8,007,764, 2011, assigned to Chevron), cycloalkyl ammoniums (Cao et al., U.S. Patent 2008/0045767, 2008, assigned to ExxonMobil; Feyen et al., WO2013/182974, 2013, assigned to BASF), N,N-dimethylpiperidinium (Yilmaz et al., WO2013/035054, 2013, assigned to BASF), and N-alkyl-1,4-diazabicyclo[2.2.2]octane cations and derivatives thereof (Zones, WO2010/114996, 2010, assigned to Chevron).

In addition to the OSDAs described above, recently the synthesis of the aluminosilicate form of CHA using choline has also been disclosed (Chen et al., Environ. Sci. Technol., 2014, 48, 13909). In said publication, the authors claim that the use of choline allows for an economical pathway to synthesise CHA. However, for the efficient synthesis of a material, and its subsequent commercial application in industry, not only the sources used in the preparation thereof must be economically appealing, but the material preparation process must also exhibit good yields. In this case, the starting Si/Al ratio of the material is 20 (as may be calculated from the experimental synthesis process of SSZ-13 described in the publication); however, the final Si/Al ratio of the crystalline solid obtained is 6.5. Said difference suggests that the synthesis yield is less than 30% (crystalline solid obtained as a function of the inorganic oxides introduced during preparation of the gel). This low yield would prevent the use of said synthesis process in potential industrial applications.

In recent years, it has been disclosed that zeolite materials with the CHA crystal structure wherein Cu cations have been incorporated (Cu-CHA) are efficient heterogeneous catalysts for the selective reduction of NOx in transport-related emissions. These catalysts show high hydrothermal stability thanks to the presence of the small pores of the CHA structure, and the stabilisation of the Cu cations in the CHA cavities. These catalysts are capable of tolerating temperatures greater than 700° C. in the presence of water.

Despite the progress observed in recent years in the synthesis of the zeolite SSZ-13 using more economical OSDAs, there is clearly still a need for the chemical industry to improve the synthesis of said crystal structure, with a view to its application in various catalytic applications, and, more particularly, its use as a catalyst and/or support in the treatment of NOx in gas emissions from automobiles.

DESCRIPTION OF THE INVENTION

The present invention relates to a new synthesis process of a zeolite with the chabazite structure (CHA), which uses a commercial and economical OSDA, as well as the subsequent use of the zeolite synthesised as a catalyst in various catalytic processes, such as methanol to olefins and the selective catalytic reduction (SCR) of NOx in gas emissions.

The present invention relates to a new synthesis process of a crystalline material with the CHA zeolite structure, which may comprise, at least, the following steps:
i) Preparation of a mixture that comprises at least one source of water, at least one source of a tetravalent element Y, at least one source of an alkaline or alkaline earth cation A, at least one source of a trivalent element X, and at least one organic molecule (OSDA1) with the structure $[R^1R^2R^3R^4N^+]Q^-$,
wherein $R^1$, $R^2$, $R^3$ and $R^4$ are selected from linear alkyl groups, and
wherein $R^1$, $R^2$, $R^3$ and $R^4$ each have between 1 and 4 carbon atoms, but at least two of them must have at least two carbon atoms, and
wherein $Q^-$ is an anion, being the molar composition:

$n\ X_2O_3{:}YO_2{:}a\ A{:}m\ OSDA1{:}z\ H_2O$ wherein
n ranges between 0 and 0.1; preferably between 0.005 and 0.1; and, more preferably, between 0.01 and 0.1.
a ranges between 0 and 2; preferably between 0 and 1; and, more preferably, between 0 and 0.8.
m ranges between 0.01 and 2; preferably between 0.1 and 1; and, more preferably, between 0.1 and 0.6.
z ranges between 1 and 200; preferably between 1 and 50; and, more preferably, between 2 and 20.

ii) Crystallisation of the mixture obtained in i) in a reactor
iii) Recovery of the crystalline material obtained in ii)

According to a particular embodiment, the source of the tetravalent element Y may be selected from silicon, tin, titanium, germanium, and combinations thereof. Preferably, the source of the element Y is a source of silicon that may be selected from silicon oxide, silicon halide, colloidal silica, fumed silica, tetraalkyl orthosilicate, silicate, silicic acid, a previously synthesised crystalline material, a previously synthesised amorphous material, and combinations thereof; and, more preferably, it is a material selected from a previously synthesised crystalline material, a previously synthesised amorphous material and combinations thereof; and, more preferably, a previously synthesised crystalline material.

Some examples of previously synthesised materials may be faujasite-type (FAU) and L-type (LTL) zeolites, and amorphous ordered mesoporous materials, such as MCM-41. These previously synthesised materials may further contain other heteroatoms in their structure, such as, for example, aluminium.

According to a particular embodiment, the source of the element Y may be a previously synthesized material, faujasite, and may contain heteroatoms in its structure, such as, for example, aluminium.

According to a preferred embodiment, the source of the trivalent element X may be selected from aluminium, boron, iron, indium, gallium and combinations thereof.

According to a particular embodiment, the trivalent element X is aluminium. Said source of aluminium may be selected from, at least, any aluminium salt (for example, aluminium nitrate) or any hydrated aluminum oxide.

According to a particular embodiment of the present invention, OSDA1 may be selected from tetraethylammonium, methyl triethylammonium, propyl triethylammonium, diethyl dipropylammonium, diethyl dimethylammonium, and combinations thereof. Preferably, said OSDA1 is tetraethylammonium.

The present invention shows the use of simple organic molecules such as OSDAs in the synthesis of zeolite with the chabazite structure, based on tetraalkylammonium cations, wherein the alkyl groups are linear chains ranging between C1 and C4, and where, at least, two of said alkyl groups are a C2 or longer linear chain.

Particularly, it is shown that the tetraethylammonium (TEA) cation allows for the synthesis of zeolite with the chabazite structure with a low economic cost, since said organic molecule is commercial and, furthermore, requires precursors that are much more economical than those required for the preparation of many of the more complex organic molecules described above for the synthesis of a zeolite with the chabazite structure. Moreover, the present process allows obtaining the desired crystalline material with high yields (greater than 80%).

According to the present invention, the crystallisation process described in ii) is preferably performed in autoclaves, under conditions that may be static or dynamic, at a temperature ranging between 100° C. and 200° C., preferably between 130° C. and 175° C., and, more preferably, between 150° C. and 175° C., and with a crystallisation time ranging between 6 hours and 50 days, preferably between 1 and 14 days, and, more preferably, between 2 and 10 days. It must be borne in mind that the components of the synthesis mixture may come from different sources, which may modify the crystallisation conditions described.

According to a particular embodiment of the process of the present invention, CHA crystals may be added to the synthesis mixture to act as seeds, thus favouring the synthesis described, in a quantity of up to 25% by weight with respect to the total quantity of oxides. These crystals may be added before or during the crystallisation process.

According to the process described, following the crystallisation described in ii), the resulting solid is separated from the mother liquour and recovered. Recovery step iii) may be performed by means of different known separation techniques, such as, for example, decantation, filtration, ultrafiltration, centrifugation or any other solid-liquid separation technique, and combinations thereof.

The process of the present invention may further comprise the elimination of the organic content retained inside the material by means of an extraction process.

According to a particular embodiment, the elimination of the organic compound retained inside the material may be performed by means of a heat treatment at temperatures greater than 25° C., preferably ranging between 100° C. and 1000° C., for a period of time preferably ranging between 2 minutes and 25 hours.

According to another particular embodiment, the material produced in accordance with the present invention may be pelletized using any known technique.

In the process described above, any cation present in the material may be exchanged with other cations by means of ion exchange using conventional techniques. Thus, depending on the $X_2O_3/YO_2$ molar ratio of the synthesised material, any cation present in the material may be exchanged, at least partially, by means of ion exchange. These exchanged cations are preferably selected from metals, protons, proton precursors (such as, for example, ammonium ions) and mixtures thereof; more preferably, said cation is a metal selected from rare earths, metals of groups IIA, IIIA, IVA, VA, IB, IIB, IIIB, IVB, VB, VIB, VIIB, and VIII, and combinations thereof.

According to a preferred embodiment, the ion exchange cation is copper.

The present invention also relates to a zeolite material with the CHA structure obtained according to the process described above, which may have the following molar composition:

wherein
X is a trivalent element;
Y is a tetravalent element;
A is an alkaline or alkaline earth cation;
o ranges between 0 and 0.1; preferably between 0.005 and 0.1; and, more preferably, between 0.01 and 0.1.
p ranges between 0 and 1, preferably between 0 and 0.8; and more preferably between 0 and 0.5.
q ranges between 0.01 and 1; preferably between 0.01 and 0.5; and, more preferably, between 0.01 and 0.3.
r ranges between 0 and 2; preferably between 0 and 1.5; and, more preferably, between 0 and 1.

According to a preferred embodiment, the material obtained according to the present invention may be calcined. Thus, the zeolite material with the CHA structure may have the following molar composition after being calcined:

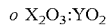

wherein
X is a trivalent element; and
Y is a tetravalent element; and
o ranges between 0 and 0.1; preferably between 0.005 and 0.1; and, more preferably, between 0.01 and 0.1.

According to a particular embodiment, the tetravalent element Y of the zeolite material with the CHA structure may be preferably selected from silicon, tin, titanium, germanium, and combinations thereof; more preferably, it is silicon.

On the other hand, the trivalent element X of the zeolite material with the CHA structure according to the present invention may be preferably selected from aluminium, boron, iron, indium, gallium and combinations thereof; more preferably, it is Al.

The material of the present invention obtained according to the process described above has the lattice structure of the zeolite CHA.

According to a particular embodiment, the crystalline material obtained is substantially free from the presence of phosphorus in the crystal lattice.

The present invention also relates to the use of the materials described above, obtained according to the process of the present invention, as catalysts for the conversion of feeds formed by organic compounds in high-added-value products, or as molecular sieves for stream elimination/separation (for example, gas mixtures), by bringing the feeds into contact with the material obtained.

According to a preferred embodiment, the material obtained in accordance with the present invention may be used in the production of olefins after bringing it into contact with an oxygenated organic compound under certain reaction conditions. Particularly, when methanol is fed, the olefins obtained are primarily ethylene and propylene. The ethylene and the propylene may be polymerised to form polymers and co-polymers, such as polyethylene and polypropylene.

According to another preferred embodiment, the material obtained in the present invention may be used as a catalyst in selective catalytic reduction (SCR) reactions of NOx (nitrogen oxides) in a gas stream. Particularly, the SCR of NOx will be performed in the presence of reducing agents, such as ammonium, urea and/or hydrocarbons. Materials which have had copper atoms introduced by means of any known technique are particularly useful for this use.

Throughout the description and the claims, the word "comprises" and variants thereof are not intended to exclude other technical characteristics, additives, components or steps. For persons skilled in the art, other objects, advantages and characteristics of the invention will arise, partly from the description and partly from the practice of the invention.

BRIEF DESCRIPTION OF THE FIGURES

FIG. 1 shows the diffraction pattern of the material obtained in Example 1 of the present invention.

The present invention is illustrated by means of the following examples, which are not intended to limit the scope of the invention.

EXAMPLES

Example 1: Synthesis of CHA Using Tetraethylammonium as the OSDA 1037.2 mg of an aqueous solution of tetraethylammonium hydroxide (TEAOH, Sigma Aldrich, 35% by weight in water) are mixed with 477.1 mg of a 20%-by-weight aqueous solution of sodium hydroxide (NaOH, Sigma-Aldrich, 98%) and 34 mg of Milli-Q water. The mixture is homogenised by being kept under stirring. Finally, 791.0 mg of zeolite Y (CBV-720, $SiO_2/Al_2O_3$ molar ratio=21) are added, and the mixture is kept under stirring until the desired concentration is achieved. The composition of the final gel is $SiO_2/0.047$ $Al_2O_3/0.2$ TEAOH/0.2 NaOH/5 $H_2O$. This gel is transferred to a teflon-lined steel autoclave and heated at 160° C. for 7 days. Once this time has elapsed, the product obtained is recovered by means of filtration and washed abundantly with water. By means of X-ray diffraction, it is observed that the solid obtained presents the characteristic peaks of the CHA structure (see FIG. 1). The solid yield obtained is greater than 85%.

The material is calcined at 550° C. for 4 h in an air atmosphere in order to eliminate the organic matter retained inside it.

Example 2: Synthesis of CHA Using Tetraethylammonium as the OSDA 4494.4 mg of an aqueous solution of tetraethylammonium hydroxide (TEAOH, Sigma Aldrich, 35% by weight in water) are mixed with 2047.1 mg of a 20%-by-weight aqueous solution of sodium hydroxide (NaOH, Sigma-Aldrich, 98%) and 9525.0 mg of Milli-Q water. The mixture is homogenised by being kept under stirring. Finally, 3670.2 mg of zeolite Y (CBV-712, $SiO_2/Al_2O_3$ molar ratio=12) are added, and the mixture is kept under stirring until the desired concentration is achieved. The composition of the final gel is $SiO_2/0.083$ $Al_2O_3/0.2$ TEAOH/0.2 NaOH/15 $H_2O$. This gel is transferred to a teflon-lined steel autoclave and heated at 160° C. for 7 days. Once this time has elapsed, the product obtained is recovered by means of filtration and washed abundantly with water. By means of X-ray diffraction, it is observed that the solid obtained presents the characteristic peaks of the CHA structure. The solid yield obtained is greater than 85%.

The material is calcined at 550° C. for 4 h in an air atmosphere in order to eliminate the organic matter.

Example 3: Synthesis of Triethylpropylammonium Hydroxide 12.8 ml of triethylamine ($C_6H_{15}N$, Sigma Aldrich, 99%) are dissolved in 250 ml of acetonitrile ($CH_3CN$, Scharlau, 99%). This solution is kept under stirring whilst 44 ml of 1-iodopropane ($C_3HI$, Sigma Aldrich, 99%) are added drop by drop. After the addition is completed, the mixture is heated under reflux at 80° C. for 3 days. Once this time has elapsed, the mixture is partially concentrated in the rotary evaporator and an excess of diethyl ether ($C_4H_{10}O$, Scharlau, 99.5%) is added in order to precipitate the final product triethylpropylammonium iodide, which is vacuum filtered and washed with diethyl ether, to obtain a yield of 88%.

Finally, ion exchange of the triethylpropylammonium halide is performed with the corresponding hydroxide. To this end, a solution of 10 g of triethylpropylammonium iodide in 73.7 g of water is prepared, and 37 g of the ion-exchange resin Amberlite (Amberlite IRN78, hydroxide form, Supelco) are added to this mixture. The mixture is kept under stirring overnight and, once this time has elapsed, it is vacuum filtered in order to separate the final product, triethylpropylammonium hydroxide, from the resin. The solution obtained is titrated with hydrochloric acid (HCl, Sigma Aldrich, 0.1 M), resulting in a concentration of 7.1% by weight and 75% exchange.

Example 4: Synthesis of CHA Using Triethyl Propylammonium as the OSDA 3064.5 mg of a solution of triethylpropylammonium hydroxide (TEPrOH, 7.1% by weight, prepared according to Example 3 of the present invention) are mixed with 274.0 mg of a 20%-by-weight solution of sodium hydroxide (NaOH, 98%) in water. The mixture is homogenised by being kept under stirring. Finally, 435.0 mg of zeolite Y (CBV-720, $SiO_2/Al_2O_3$ molar ratio=21) are added, and the mixture is kept under stirring until the desired concentration is achieved. The composition of the final gel is $SiO_2/0.047$ $Al_2O_3/0.2$ TEPrOH/0.2 NaOH/5 $H_2O$. This gel is transferred to a teflon-lined steel autoclave and heated at 160° C. for 7 days. Once this time has elapsed, the product obtained is recovered by means of filtration and washed abundantly with water. By means of X-ray diffraction, it is observed that the solid obtained primarily presents the characteristic peaks of the CHA structure.

The material is calcined at 550° C. for 4 h in an air atmosphere in order to eliminate the organic matter.

Example 5: Preparation of the Cu-Exchanged Zeolite CHA (Cu-CHA)

The sample synthesised and calcined according to the method explained in Example 1 is washed with 150 g of a 0.04 M aqueous solution of sodium nitrate ($NaNO_3$, Fluka, 99% by weight) per gram of zeolite.

33.63 mg of copper acetate [$(CH_3COO)_2Cu.H_2O$, Probus, 99%] are dissolved in 30 g of water, and 303.3 mg of the previously washed zeolite are added. The suspension is kept under stirring for 24 h. Once this time has elapsed, the product obtained is recovered by means of filtration and washed abundantly with water. Finally the material is calcined in air at 550° C. for 4 h.

Example 6: Catalytic Assay of the SCR Reaction of NOx

The catalytic activity of the Cu-CHA sample synthesised according to Example 5 of the present invention in the selective catalytic reduction of NOx is studied using a fixed-bed tubular quartz reactor 1.2 cm in diameter and 20 cm long. In a typical experiment, the catalyst is compacted into particles with a size ranging between 0.25-0.42 mm; these are introduced into the reactor and the temperature is increased until 550° C. are reached (see the reaction conditions in Table 1); subsequently, this temperature is maintained for one hour under a flow of nitrogen. Once the desired temperature has been reached, the reaction mixture is fed. The SCR of NOx is studied using $NH_3$ as the reducing agent. The NOx present in the reactor outlet gas is continuously analysed by means of a chemiluminescent detector (Thermo 62C).

TABLE 1

| Reaction conditions for the SCR of NOx | |
|---|---|
| Total gas flow (ml/min) | 300 |
| Catalyst load (mg) | 40 |
| NO concentration (ppm) | 500 |
| $NH_3$ concentration (ppm) | 530 |
| $O_2$ concentration (%) | 7 |
| $H_2O$ concentration | 5 |
| Tested temperature range (° C.) | 170-550 |

The catalytic results of the Cu-CHA catalyst prepared according to Example 5 of the present invention are summarized in Table 2.

TABLE 2

Conversion (%) of NOx at different temperatures (200° C., 250° C., 300° C., 350° C., 400° C., 450° C., 500° C.) using the Cu-CHA catalyst prepared according to Example 5 of the present invention
Conversion (%) of NOx at different temperatures

|  | 210° C. | 250° C. | 300° C. | 350° C. | 400° C. | 450° C. | 500° C. | 550° C. |
|---|---|---|---|---|---|---|---|---|
| Example 5 | 94.9 | 100.0 | 100.0 | 100.0 | 100.0 | 99.7 | 95.5 | 90.8 |

The invention claimed is:

1. A process of synthesizing a crystalline material with the CHA zeolite structure comprising, at least, the following steps:
   i) Preparation of a mixture that comprises at least one source of water, at least one source of a tetravalent element Y, at least one source of an alkaline or alkaline earth cation A, at least one source of a trivalent element X, and at least one organic molecule (OSDA1) with the structure $[R^1R^2R^3R^4N^+]Q^-$,
   wherein the tetravalent element Y is silicon, and
   wherein the trivalent element X is aluminium, and
   wherein the source of the tetravalent element Y and the trivalent element X comprises faujasite
   wherein $R^1$, $R^2$, $R^3$ and $R^4$ are selected from linear alkyl groups, and wherein $R^1$, $R^2$, $R^3$ and $R^4$ each have between 1 and 4 carbon atoms, but at least two of them must have at least two carbon atoms, and wherein $Q^-$ is an anion, and
   wherein the OSDA1 is selected from tetraethylammonium, methyl triethylammonium, propyl triethylammonium, diethyl dipropylammonium, diethyl dimethylammonium, and combinations thereof, the mixture being the molar composition:

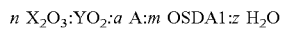
   $n\ X_2O_3{:}YO_2{:}a\ A{:}m\ OSDA1{:}z\ H_2O$ wherein
   n ranges between 0.005 and 0.1;
   a ranges between 0 and 2;
   m ranges between 0.01 and 2;
   z ranges between 1 and 200;
   ii) Crystallization of the mixture obtained in i) in a reactor
   iii) Recovery of the crystalline material obtained in ii).

2. The process according to claim 1, wherein the source of the tetravalent element Y is a source of silicon selected from silicon oxide, silicon halide, colloidal silica, fumed silica, tetraalkyl orthosilicate, silicate, silicic acid, a previously synthesised crystalline material, a previously synthesised amorphous material, and combinations thereof.

3. The process according to claim 1, wherein the source of silicon is selected from a previously synthesised crystalline material, a previously synthesised amorphous material and combinations thereof.

4. The process according to claim 3, wherein the previously synthesised materials contain other heteroatoms in their structure.

5. The process according to claim 4, wherein said OSDA1 is tetraethylammonium.

6. The process according to claim 1, wherein the crystallization process described in ii) is performed in autoclaves, under static or dynamic conditions.

7. The process according to claim 1, wherein the crystallization process described in ii) is performed at a temperature ranging between 100° C. and 200° C.

8. The process according to claim 1, wherein the crystallization time of the process described in ii) ranges between 6 hours and 50 days.

9. The process according to claim 1, further comprising the addition of CHA crystals to the synthesis mixture, as seeds, in a quantity of up to 25% by weight with respect to the total quantity of oxides.

10. The process according to claim 9, wherein the CHA crystals are added before the crystallization process or during the crystallization process.

11. The process according to claim 1, wherein recovery step iii) is performed by means of a separation technique selected from decantation, filtration, ultrafiltration, centrifugation, and combinations thereof.

12. The process according to claim 1, wherein it further comprises the elimination of the organic content retained inside the material by means of an extraction process.

13. The process according to claim 1, wherein it further comprises the elimination of the organic content retained inside the material by means of a heat treatment at temperatures ranging between 100° C. and 1000° C. for a period of time ranging between 2 minutes and 25 hours.

14. The process according to claim 1, wherein the material obtained is pelletized.

15. The process according to claim 1, wherein any cation present in the material may be exchanged with other cations by means of ion exchange.

16. The process according to claim 15, wherein the exchanged cation is selected from metals, protons, proton precursors, and mixtures thereof.

17. The process according to claim 16, wherein the exchanged cation is a metal selected from rare earths, metals of groups IIA, IIIA, IVA, VA, IB, IIB, IIIB, IVB, VB, VIB, VIIB, and VIII, and combinations thereof.

18. The process according to claim 17, wherein the metal is copper.

19. A method for converting, eliminating, or separating feeds formed by organic compounds in a high-added-value product, which comprises bringing said feed into contact with a zeolite material with the CHA structure made according to the process of claim 1.

20. A method of producing an olefin, which comprises contacting an oxygenated organic compound with a zeolite material with the CHA structure made according to the process of claim 1.

21. A method of selective catalytic reduction (SCR) of NOx (nitrogen oxides) in a gas stream, which comprises contacting the gas stream with a zeolite material with the CHA structure made according to the process of claim 1.

22. A zeolite material with the CHA structure obtained according to the process described in claim 1, wherein it has the following molar composition:

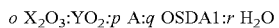
$o\ X_2O_3{:}YO_2{:}p\ A{:}q\ OSDA1{:}r\ H_2O$ wherein
X is a trivalent element;
Y is a tetravalent element;
A is an alkaline or alkaline earth cation;
o ranges between 0.005 and 0.1;
p ranges between 0 and 1;
q ranges between 0.01 and 1; and
r ranges between 0 and 2, and
wherein the tetravalent element Y is silicon, and
wherein the trivalent element X is aluminium, and
wherein the source of the tetravalent element Y and the trivalent element
X comprises faujasite,
wherein the OSDA1 is selected from tetraethylammonium, methyl triethylammonium, propyl triethylammonium, diethyl dipropylammonium, diethyl dimethylammonium, and combinations thereof.

23. The zeolite material with the CHA structure according to claim 22, having the following molar composition after being calcined:

$$o\, X_2O_3:YO_2$$

where
X is aluminium;
Y is silicon; and
wherein the source of the tetravalent element Y and the trivalent element X comprises faujasite,
n ranges between 0.005 and 0.1.

24. The zeolite material with the CHA structure according to claim 23, wherein the tetravalent element Y additionally contains, tin, titanium, germanium, and combinations thereof.

25. The zeolite material with the CHA structure according to claim 23, wherein the trivalent element X additionally contains, boron, iron, indium, gallium, and combinations thereof.

* * * * *